United States Patent [19]

Berg

[11] Patent Number: 5,423,955
[45] Date of Patent: Jun. 13, 1995

[54] SEPARATION OF PROPYLENE GLYCOL FROM 1,2-BUTANEDIOL BY AZEOTROPIC

[75] Inventor: Lloyd Berg, 1314 S. Third Ave., Bozeman, Mont. 59715

[73] Assignee: Lloyd Berg, Bozeman, Mont.

[21] Appl. No.: 270,751

[22] Filed: Jul. 5, 1994

[51] Int. Cl.⁶ .................. B01D 3/36; C07C 29/82; C07C 31/20
[52] U.S. Cl. ........................ 203/68; 203/69; 203/70; 568/868
[58] Field of Search .............. 203/52, 68, 69, 70; 568/868

[56] References Cited

U.S. PATENT DOCUMENTS

| 4,028,195 | 6/1977 | Becker et al. | 203/60 |
| 4,935,102 | 6/1990 | Berg | 203/69 |
| 4,966,658 | 10/1990 | Berg | 203/69 |
| 4,980,033 | 12/1990 | Berg | 203/68 |

Primary Examiner—Wilbur Bascomb, Jr.

[57] ABSTRACT

Propylene glycol is difficult to separate from 1,2-butanediol by conventional distillation or rectification because of the proximity of their boling points. Propylene glycol can be readily separated from 1,2-butanediol by azeotropic distillation. Effective agents are 2,2-dimethyl butane, 3-carene and diethyl benzene.

1 Claim, No Drawings

SEPARATION OF PROPYLENE GLYCOL FROM 1,2-BUTANEDIOL BY AZEOTROPIC

FIELD OF THE INVENTION

This invention relates to a method for separating propylene glycol from 1,2-butanediol using certain organic liquids as the agent in azeotropic distillation.

DESCRIPTION OF PRIOR ART

Azeotropic distillation is the method of separating close boiling compounds or azeotropes from each other by carrying out the distil in a multiplate rectification column in the presence of an added l said liquid forming an azeotrope with one or both of the compounds t separated. Its presence on each plate of the rectification column alters the relative volatility in a direction to make the separati on each plate greater and thus require either fewer plates to effe the same separation or make possible a greater degree of separatio with the same number of plates. The azeotrope forming agent is introduced with the feed to a continuous column. The azeotrope forming agent and the more volatile component are taken off as ove product and the less volatile component comes off as bottoms produ The usual methods of separating the azeotrope former from the more volatile component are cooling and phase separation or solvent extraction.

There are a number of commercial processes which produce complex mixtures of glycols, e.g. the catalytic hydrocracking of sugars and starches. These processes usually produce a homologous series of glycols. Two of the commonest glycols usually present are propylene glycol and 1,2-butanediol. Propylene glycol boils at 187° C. and 1,2-butanediol boils at 192° C. The relative volatility between these two is 1.15 which makes it very difficult to separate them by conventional rectification. Azeotropic distillation would be an attractive method of effecting the separation of propylene glycol fro 1,2-butanediol if agents can be found that (1) will create a large apparent relative volatility between propylene glycol and 1,2-butaned and (2) are easy to recover from propylene glycol. Table 1 shows the relative volatility required to obtain 99% purity. With no agent, the relative volatility is 1.15 and 88 actual plates are required. With an agent giving a relative volatility of 2, only 19 plates are required.

OBJECTIVE OF THE INVENTION

The object of this invention is to provide a process or method of azeotropic distillation that will enhance the relative volatility of propylene glycol from 1,2-butanediol in their separation in a rectification column. It is a further object of this invention to identify organic compounds which in addition to the above constrain are stable, can be separated from propylene glycol and recyled to t azeotrope column with little decomposition.

TABLE 1

Theoretical and Actual Plates Required vs. Relative Volatility for Propylene Glycol - 1,2-Butanediol Separation

| Relative Volatility | Theoretical Plates Required At Total Reflux, 99% Purity | Actual Plates Required 75% Efficiency |
|---|---|---|
| 1.15 | 66 | 88 |
| 1.5 | 23 | 31 |
| 2.0 | 14 | 19 |
| 3.0 | 9 | 12 |
| 3.5 | 8 | 11 |

SUMMARY OF THE INVENTION

The objects of this invention are to provide a process for separating propylene glycol from 1,2-butanediol which entails the use of certain organic compounds as the agent in azeotropic distillation.

DETAILED DESCRIPTION OF THE INVENTION

I have discovered that certain organic compounds will greatly improv the relative volatility of propylene glycol to 1,2-butanediol and permit the separation of propylene glycol from 1,2-butanediol by rectification when employed as the agent in azeotropic distillation. Table 2 lists the compounds that I have found to be effective. They are pentane, toluene, ethyl benzene, o-xylene, p-xylene, cumene, m-diisopropyl benzene, diethylbenzene, mesitylene, p-cymene, hexane, cyclohexane, methyl cyclohexane, heptane, 3-methyl pentane, octane, decane, 2,3,4-trimethyl pentane, dipentene, decalin, dicyclopentadie alpha-phellandrene, limonene, hemimellitene, myrcene, terpinolene, p-mentha-1,5-diene, beta-pinene, 3-carene, 1-heptene, cyclopentane, o-diethyl benzene, 2,2-dimethyl butane and 2-methylbutane.

THE USEFULNESS OF THE INVENTION

The usefulness or utility of this invention can be demonstrated by referring to the data presented in Tables 1 and 2. All of the successful agents show that propylene glycol can be separated from 1,2-butanediol by means of azeotropic distillation in a rectificati column and that the ease of separation as measured by relative volatility is considerable.

WORKING EXAMPLES

Example 1

Twenty-seven grams of propylene glycol, 13 grams of 1,2-butanediol and 40 grams of 2,2-dimethyl butane were charged to a vapor-liquid equilibrium still and refluxed for four hours. Analysis indicated a vapor composition of 93.5% propylene glycol, 6.5% 1,2-butanediol; a liquid composition of 87.7% propylene glycol, 12.3% 1,2-butanediol. This is a relative volatility of 2.0.

TABLE 2

Effective Azeotropic Distillation Agents For Separating Propylene Glycol From 1,2-Butanediol

| Compounds | Relative Volatility |
|---|---|
| None | 1.15 |
| Toluene | 1.4 |
| Ethyl benzene | 2.0 |
| o-Xylene | 2.0 |
| p-Xylene | 1.5 |
| Cumene | 2.0 |
| m-Diisopropyl benzene | 1.4 |
| m-Diethyl benzene | 2.0 |
| Mesitylene | 2.0 |
| p-Cymene | 2.0 |
| Hexane | 2.0 |

TABLE 2-continued

Effective Azeotropic Distillation Agents For
Separating Propylene Glycol From 1,2-Butanediol

| Compounds | Relative Volatility |
|---|---|
| Cyclohexane | 1.3 |
| Methyl cyclohexane | 2.0 |
| Heptane | 1.5 |
| 3-Methyl pentane | 2.0 |
| Octane | 1.6 |
| Decane | 1.9 |
| 2,3,4-Trimethyl pentane | 2.0 |
| Dipentene | 2.0 |
| Decalin | 1.8 |
| Dicyclopentadiene | 1.25 |
| alpha-Phellandrene | 2.0 |
| Limonene | 1.43* |
| Hemimellitene | 2.0 |
| Myrcene | 1.29* |
| Terpinolene | 1.27* |
| p-Mentha-1,5-diene | 2.0 |
| beta-Pinene | 1.30* |
| 3-Carene | 1.42* |
| 1-Heptene | 2.0 |
| Cyclopentane | 2.0 |
| Pentane | 1.6 |
| o-Diethyl benzene | 2.0 |
| 2,2-Dimethyl butane | 2.0 |
| 2-Methyl butane | 1.5 |

*Data Obtained in Multiplate Rectification Column

Example 2

Fifty grams of propylene glycol, 50 grams of 1,2-butanediol and 140 grams of 3-carene were placed in the stillpot of a 5.6 theoretical plate glass perforated plate rectification column and refluxed for 3.5 hours. The overhead composition was 81.3% propylene glycol and 18.7% 1,2-butanediol; the bottoms composition was 37.5% propylene glycol, 62.5% 1,2-butanediol. This is a relative volatility of 1.42.

I claim:

1. A method for recovering propylene glycol from a mixture of propylene glycol and 1,2-butanediol which comprises distilling a mixture of propylene glycol and 1,2-butanediol in the presence of an azeotrope forming agent, recovering the propylene glycol and the azeotrope forming agent as overhead product and obtaining the 1,2-butanediol as bottoms product, wherein said azeotrope forming agent agent consists of one material selected from the group consisting of toluene, ethyl benzene, o-xylene, p-xylene, cumene, m-diisopropyl benzene, m-diethyl benzene, mesitylene, p-cymene, hexane, cyclohexane, methyl cyclohexane, heptane, 3-methyl pentane , octane, decane, 2,3,4-trimethyl pentane, dipentene, decalin, dicyclopentadiene, alpha-phellandrene, limonene, hemimellitene, myrcene, terpinolene, p-mentha-1,5-diene, beta-pinene, 3-carene, 1-heptene, cyclopentane, pentane, o-diethyl benzene, 2,2-dimethyl butane and 2-methyl butane.

* * * * *